United States Patent [19]

Huang et al.

[11] Patent Number: 4,576,036
[45] Date of Patent: Mar. 18, 1986

[54] METHOD AND APPARATUS FOR DETERMINING QUALITY AND MASS FLOW RATE OF FLOWING STEAM

[75] Inventors: Wann-Sheng Huang; Donald S. Mims; Richard S. Allen, all of Houston, Tex.

[73] Assignee: Texaco Inc., White Plains, N.Y.

[21] Appl. No.: 606,789

[22] Filed: May 3, 1984

[51] Int. Cl.⁴ .............................................. G01N 25/60
[52] U.S. Cl. ..................................... 73/29; 73/861.58
[58] Field of Search ........... 73/861.01, 861.02, 861.03, 73/29, 861.58; 364/510; 374/42

[56] References Cited

U.S. PATENT DOCUMENTS 4,028,942  6/1977  Gardiner ................................. 73/29
4,193,290  3/1980  Sustek et al. ........................... 73/29

Primary Examiner—Donald O. Woodiel
Attorney, Agent, or Firm—Robert A. Kulason; James J. O'Loughlin; F. C. Armistead

[57] ABSTRACT

A method based on an orifice flow equation is provided for determining both the quality and the mass flow rate of steam flowing in a line, such as to an injection well in steam flooding operations for recovery of petroleum. A sample of the steam is drawn off from the steam line through an orifice and is condensed and collected. The mass of sample collected and the time to collect it give the mass flow rate of the sample. Pressure and temperature measurements at the sample line orifice together with the measured mass flow rate of the sample and with known constants are used in the orifice flow equation to derive the sample steam quality. The line steam also flows through an orifice, with pressure and temperature measurements thereon. The desired quality of the line steam is the same as the derived quality of the sample steam, since care is taken to make them the same. The orifice flow equation is used again, substituting the derived sample steam quality for the line steam quality, together with the temperature and pressure measurements at the steam line orifice and with known constants, to derive the desired mass flow rate of the line steam.

9 Claims, 2 Drawing Figures

METHOD AND APPARATUS FOR DETERMINING QUALITY AND MASS FLOW RATE OF FLOWING STEAM

FIELD OF THE INVENTION

This invention concerns a method and apparatus for determining the quality of a liquid-vapor mixture, i.e. the proportion of vapor in the mixture and also the mass flow rate of the mixture, and more particularly for determining the quality and mass flow rate of steam in a flow line to an injection well in a steam flooding project for oil recovery.

BACKGROUND OF THE INVENTION

In the operation of steam flooding to stimulate production of oil from oil reservoirs it is important to have a simple and accurate method to determine the quality and mass flow rate of steam at the well head of an injection well. In such a stimulation process the amount of heat input to the reservoir determines the rate and amount of oil recovery, and heat input depends directly upon the steam quality and mass flow rate. Steam that is generated for injection into the reservoir generally arrives at the well head as wet steam, i.e., a mixture of vapor and liquid, at super-atmospheric pressure. A given mass of dry steam, i.e. steam of 100% quality, has a higher heat content than the same mass of wet steam at the same temperature and pressure. The greater the steam quality and the the mass flow rate are, the more the heat input to the reservoir will be. Steam quality and mass flow rate thus directly affect the rate and the ultimate amount of recovery of oil, and therefore have a bearing upon earnings and investment requirements.

Heretofore, steam quality measurements of the steam in a line to an injection well have been made using throttling orifices, making various temperature, pressure, and flow measurements, and calculating the quality of the steam in the line. This necessitated the use of a substantial piece of equipment. However it has been found that when there are several separate lines coming off one distribution manifold, each line going to a different injection well, one cannot rely on the steam quality measured in the manifold to represent the quality in any of the separate lines to the wells. In the case of a manifold having T joints, for example, the steam that has turned a corner will have a higher quality than the steam that has continued moving in a straight line, all other things being equal, since the greater momentum of the liquid phase compared to the vapor phase will result in mechanical separation of the liquid and vapor components and a higher liquid content in the straight line component. Consequently, it has heretofore been impossible to know the quality in the separate lines to the different injection wells from one quality determination at the manifold and it has been impractical to make a quality determination on each separate line using a substantial piece of equipment for each such line.

It is therefore highly desirable to have a relatively simple method and apparatus to make separate steam quality and mass flow rate determinations on each of the individual lines to separate injection wells in order to know the rate of heat input to the reservoir through each separate injection well.

BRIEF SUMMARY OF THE INVENTION

One way using relatively simple apparatus to determine steam quality is by use of orifice flow measurements and an orifice flow equation for the quality of steam in two-phase flow through such orifices. Steam containing liquid and vapor phases is passed through an orifice in a pipe, and measurements are made of the temperature, the pressure in the pipe, and the orifice differential pressure. By means of an equation relating the temperature and these two pressure measurements and other quantities available from handbooks and publications and from the dimensions of the apparatus, one can determine the quality of the steam in the pipe provided the total two-phase mass flow rate is known. Ordinarily however the mass flow rate is not known and cannot be determined unless the quality of the steam is known. Thus an impasse ordinarily results, in which the quality cannot be determined without knowing the mass flow rate, and the mass flow rate cannot be determined without knowing the quality. In the present invention this impasse is broken in the way described herein, resulting in the determination not only of the steam quality but also of the mass flow rate.

Two separate and distinct sets of orifice flow measurements are made, one within the steam line to an injection well, in which line one orifice plate is installed, and the other within a sample conduit which draws off a representative sample of the steam through another orifice plate. The total mass flow rate in the sample conduit is measured directly by condensing the vapor therein and collecting the combined liquid and condensed vapor components. The mass of the collected sample and the time to collect it are measured, giving the total mass flow rate of the vapor and liquid in the sample conduit. Having this mass flow rate and the sample conduit orifice temperature and pressure measurements, one can determine the quality of the steam in the sample using the orifice flow equation.

Since the steam sample is representative of the steam in the line, the thus-determined steam sample quality is also the line steam quality, which is an object of this invention.

Further, using this line steam quality value together with the steam line orifice temperature and pressure measurements and the same orifice flow equation as above, one can determine the total mass flow rate in the steam line, which is another object of this invention.

Moreover, these determinations of line steam quality and mass flow rate are made using relatively simple method and apparatus, thus achieving still another object of this invention.

BRIEF DESCRIPTION OF THE DRAWINGS

The foregoing and other objects and benefits of the invention will be more fully set forth below in connection with the best mode contemplated by the inventors of carrying out the invention, and in connection with which there are illustrations provided in the drawings, wherein.

DESCRIPTION OF THE PREFERRED EMBODIMENT

Figure 1:
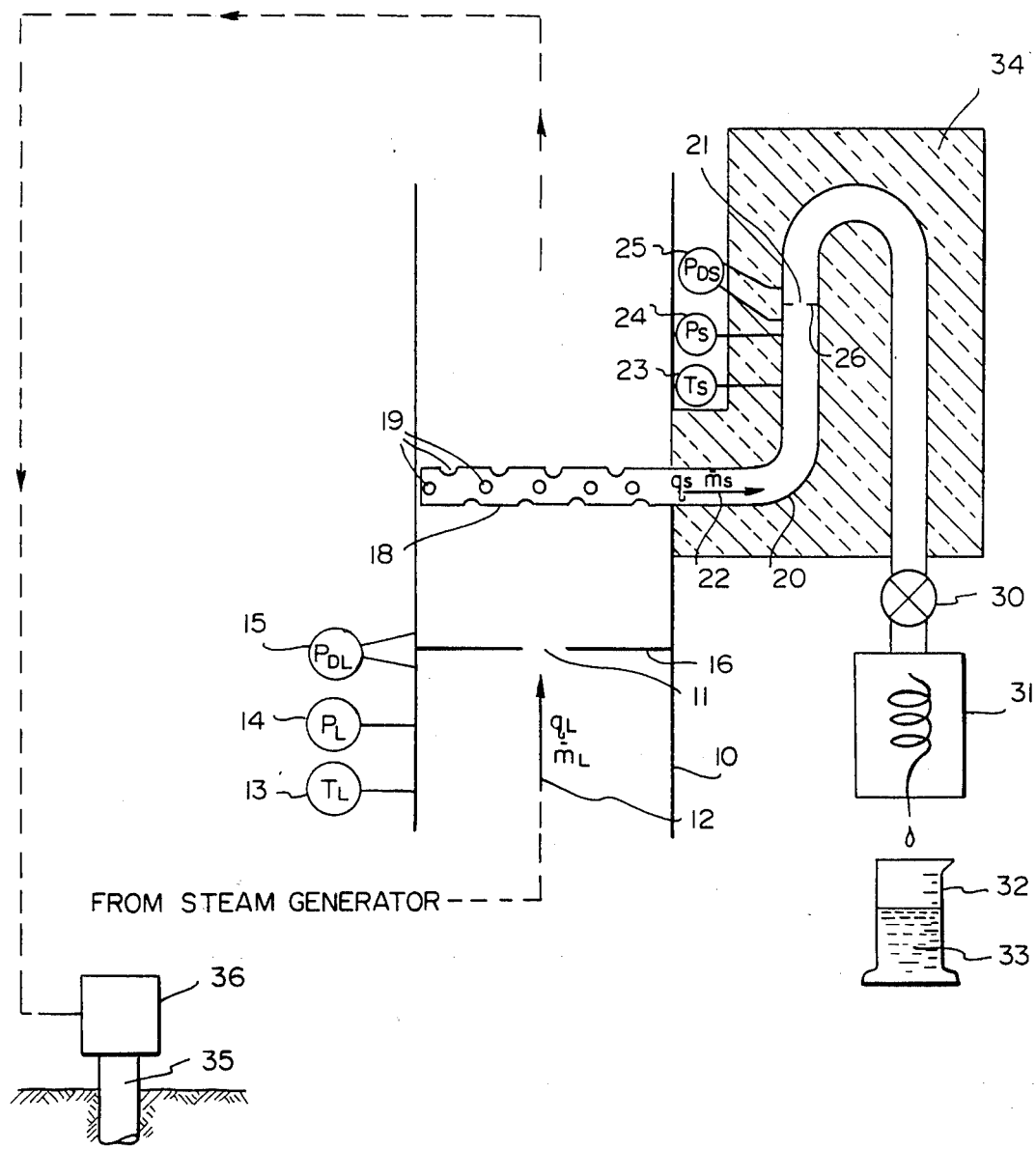
FIG. 1 of the drawings is a schematic representation of a steam flow line to an injection well together with elements that are employed in order to carry out the method according to the invention.

It is well known that the quality and the mass flow rate of steam flowing through an orifice are interdependent quantities; one cannot be determined without first knowing the other. However if one knows for example the mass flow rate and measures the temperature and the pressure of the steam and the pressure difference across the orifice, one can solve an equation relating these quantities and known constants to derive the quality of the steam. Conversely, if one knows the quality of the steam and makes the same measurements one can solve the same equation to derive the mass flow rate.

The equation relating these quantities to each other is set forth in a paper by D. B. Collins and M. Gacesa, Journal of Basic Engineering, Trans. ASME, Vol. 93, March 1971 (hereinafter Reference 1). Certain known constants required in the equation are identified in another reference, "Principles and Practice of Flow Meter Engineering" by L. K. Spink, 8th Edition, Foxboro Co. Publisher (hereinafter Reference 2).

The form of the equation is $$q = \frac{-R}{Q} + D_2 \frac{kd^2}{Q}(10^8 y)^{\frac{1}{2}} + D_3 \left[\frac{kd^2}{Q}(10^8 y)^{\frac{1}{2}}\right]^2 \quad (1)$$

Where:
q = quality (mass of vapor)/(mass of vapor + liquid)

$$Q = \frac{D_1}{x} - R$$

R = square root of vapor to liquid density ratio, a function of operating temperature T
$D_1, D_2, D_3$ = empirical constants derived from curve fit
k = orifice plate flow coefficient
d = orifice throat diameter (inches)
x = net expansion factor $$y = \frac{P_d D_V}{m^2}$$

P = static pressure
$P_d$ = orifice differential pressure (inches water)
$D_V$ = vapor density, pounds mass/ft$^3$, a function of operating temperature T
m = two-pase mass flow rate, pounds mass/hr.
Reference 1 listed $D_1 = 1.275$ $D_2 = 0.03066$ $D_3 = 0.0006586$ Orifice flow coefficient k can be expressed as $k = k_L F_a F_r$ where:
$k_L$ = orifice discharge coefficient for liquid flow
$F_a$ = areal temperature correction, a function of operating temperature T
$F_r$ = Reynolds number correction for steam
$k_L$ is given as $k_L = 0.598 + 0.01r + 1.947(10^{-5})(10r)^{4.425}$ with r defined as orifice throat dia./pipe inside dia.
$F_a$ as given in Reference 2, Page 147 as a function of orifice material and operating temperature T
$F_r$ is given in Reference 2 as $F_r = 1 + E/R_d$ Where:
E = a function of (r, and pipe dia.) Reference 2, page 374
$R_d$ = Reynolds number based on orifice throat size
Reference 2, page 336 gives x = a function of (r, and $P_d/P$)

It can be seen from equation 1 that the quality of steam flowing through an orifice is a function of static pressure, orifice differential pressure, temperature, two-phase mass flow rate, and constants from handbooks, apparatus dimensions, and References 1 and 2. This is expressed mathematically as $$q = f_1(P, P_D, T, \dot{m}, \text{constants}) \quad (2)$$

Similarly the two-phase mass flow rate of steam flowing through an orifice is another function, derived from the above equation, of static pressure, orifice differential pressure, temperature, quality and constants from handbooks, apparatus dimensions, and References 1 and 2. This is expressed mathematically as $$\dot{m} = f_2(P, P_D, T, q, \text{constants}). \quad (3)$$

In this invention steam, which is generated for injection into a well and which contains the two phases of liquid and vapor, is passed through two different orifices, one of which is in the line to the well and one in a sample conduit off to the side of the line to the well. A series of measurements are made which are then used with equations (2) and (3) to determine both the two-phase mass flow rate of steam and the quality of the steam that is being injected into the well.

FIG. 1 is a schematic illustration of equipment for carrying out the method of this invention. Steam line 10 has super-atmospheric pressure steam 12 flowing therein, having quality $q_L$ and two-phase mass flow rate $\dot{m}_L$, for injection into a well 35 having a well-head 36. Steam 12 passes vertically upward through orifice 11 in orifice plate 16, across which the steam line differential pressure $P_{DL}$ is measured by steam line orifice pressure difference measurement means 15. Flow through orifice 11 is preferred to be vertically upward to assure consistent results. Steam line static pressure $P_L$ and temperature $T_L$ are also measured by steam line pressure measurement means 14 and steam line temperature measurement means 13 respectively. A steam sampling probe 18 extends through the wall of steam line 10 and diametrically across steam line 10, having openings 19 through which a steam sample 22, having quality representative of the quality of the line steam, can be taken for drawing off through steam sample conduit 20 with which probe 18 communicates. Steam sample 22 has quality $q_s$ and two-phase mass flow rate $\dot{m}_s$. Openings 19 are advantageously staggered in location along probe 18 so that a truly representative sample of steam 12 can be taken—i.e. $q_s$ will be substantially the same as $q_L$.

Steam sampling probe 18 is activated by opening valve 30 in steam sample conduit 20, allowing steam 12, which is at super-atmospheric pressure, to flow into probe 18 through openings 19, along steam sample conduit 20 as steam sample 22, vertically upward through a sample conduit orifice 21 in orifice plate 26, through valve 30, and through a condenser 31. Flow through orifice 21 is preferred to be upwardly vertical to assure consistent results. Condenser 31 converts the vapor portion of steam sample 22 to liquid, and the total liquid sample 33, consisting of the liquefied vapor portion of steam sample 22 as well as the liquid portion thereof, is collected in sample collector 32, and its mass is measured. The time to collect sample 33 is measured as by a stopwatch. Sample conduit orifice differential pressure $P_{DS}$ is measured by sample conduit orifice pressure difference measurement means 25, and sample conduit static pressure $P_S$ and temperature $T_S$ are measured by sample conduit pressure measurement means 24 and sample conduit temperature measurement means 23, respectively. It will be remembered that sample steam quality $q_S$ is substantially the same as line steam quality $q_L$.

Steam sample conduit 20 is surrounded with thermal insulation 34 for the purpose of maintaining the steam sample conduit at the same temperature as steam line 10 in order to avoid condensation of any of the vapor component of steam sample 22 within sample conduit 20. Such condensation, if it should occur, would make steam sample quality $q_S$ no longer the same as line steam quality $q_L$.

The procedure for using the equipment of FIG. 1 to carry out the method of this invention is as follows. With super-atmospheric pressure steam 12 flowing in steam line 10, open valve 30 in sample conduit 20. Allow steam to flow through the sample conduit until a steady state flow condition is reached, such that conduit 20 and orifice 21 are sufficiently heated to minimize condensation. Measure $T_L$, $P_L$, $P_{DL}$, $T_S$, $P_S$, and $P_{DS}$. Collect liquid sample 33 in sample collector 32 and measure the time of collection as well as the mass of sample 33. Calculate the two-phase flow rate $\dot{m}_S$ for sample conduit steam 22 from the measured mass and time. Calculate $q_S$ for sample conduit steam 22 using the measured values of $T_S$, $P_S$, $P_{DS}$, and $\dot{m}_S$ and the constants as in equation (2) above. Substitute the calculated value of sample conduit steam quality for line steam quality $q_L$ in the orifice flow equation and calculate the two-phase mass flow rate $\dot{m}_L$ for line steam 12, using the measured values of $T_L$, $P_L$, and $P_{DL}$, and the constants as in equation (3) above. By this procedure both the desired line steam quality $q_L$ and the desired line steam two-phase mass flow rate $\dot{m}_L$ are determined.

Figure 2:
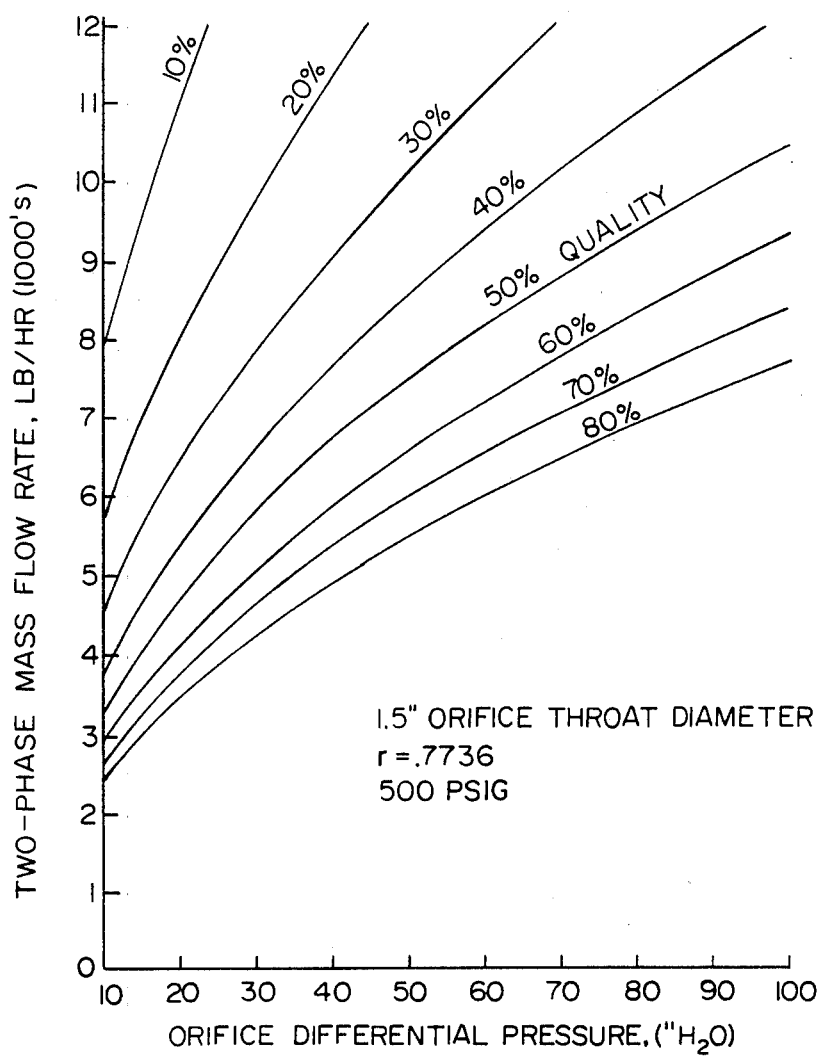
FIG. 2 is a graphical representation of two-phase steam mass flow rate as a function of orifice differential pressure for several different values of steam quality in one typical set of conditions of pressure, orifice size, and pipe size.

Calculations outlined above can, of course, be carried out by a computer programmed for this purpose. FIG. 2 was computed by such a program and presents graphically the relationships between quantities with which this invention is concerned in one typical situation. Such graphical presentations are particularly useful in field operations and can readily be prepared for the range of situations likely to be encountered. In the example represented by FIG. 2 it can be seen that steam quality is readily determined from the graph using the measured orifice differential pressure and the measured two-phase mass flow rate in one typical situation where orifice throat diameter $d = 1.5''$, ratio r of orifice throat diameter to pipe inside diameter $= 0.7736$, and static operating pressure $P = 500$ PSIG.

While particular embodiments of the invention have been described above in accordance with the applicable statutes this is not to be taken as in any way limiting the invention but merely as being descriptive thereof. All such embodiments are intended to be included within the scope of the invention which is to be limited only by the following claims.

We claim:

1. In a procedure utilizing steam of quality q flowing at mass flow rate $\dot{m}$ (m-dot), a method of determining one of q and m when the other is known, comprising:

passing said steam through an orifice-containing conduit, determining a plurality of properties of said steam in said conduit, and deriving one of q and $\dot{m}$ from an equation relating said determined steam properties to the other of said q and m.

2. In a steam injection procedure for recovering oil by introducing steam of quality q at mass flow rate m ($\dot{m}$-dot) into an injection well, a method of determining one of q and m when the other is known, comprising:

passing said steam through an orifice-containing conduit, determining a plurality of properties of said steam in said conduit, and deriving one of q and $\dot{m}$ from an equation relating said determined steam properties to the other of said q and $\dot{m}$.

3. A method for determining the quality of steam containing both liquid and vapor components comprising the steps of passing said steam through an orifice-containing conduit, determining a plurality of properties of said steam in said conduit, including at least the total mass flow rate of the combined liquid and vapor components thereof, and deriving the quality of said steam from an equation relating said determined steam properties to said quality.

4. A method for determining the quality of steam which occupies a vessel or the like, said steam containing both liquid and vapor components, said vessel having an orifice-containing sample conduit connected thereto through which is withdrawn from said vessel a sample of said steam having substantially the same quality as said steam in said vessel, comprising the steps of determining a plurality of properties of said sample steam, including at least the total mass flow rate of the combined liquid and vapor components thereof, and deriving the quality of said sample steam from an equation relating said determined steam properties to said quality, the desired steam quality of said steam within said vessel being substantially the same as the derived quality of said sample steam.

5. A method for determining the quality and the total mass flow rate of steam flowing in an orifice-containing steam line, said steam containing both liquid and vapor components, said steam line having an orifice-containing sample conduit connected thereto through which is withdrawn from said steam line a sample of said steam having substantially the same quality as said line steam, comprising the steps of determining a plurality of properties of said sample steam, including at least the total mass flow rate of the combined liquid and vapor components thereof, deriving the quality of said sample steam from an equation relating said determined sample steam properties to said quality, the desired quality of said line steam being substantially the same as the derived quality of said sample steam, determining a plurality of properties of said line steam, and deriving the desired total mass flow rate of said line steam from an equation relating said determined line steam properties and the herein derived line steam quality to said total mass flow rate of said line steam.

6. In a steam injection procedure for recovering oil by introducing steam into an injection well, a method for determining the quality and the total mass flow rate of steam flowing in an orifice-containing steam line, said steam containing both liquid and vapor components, said steam line having an orifice-containing sample conduit connected thereto through which is withdrawn from said steam line a sample of said steam having substantially the same quality as said line steam, comprising the steps of measuring the pressure of said sample steam in said sample conduit, measuring the pressure difference across said orifice in said sample conduit, measuring the temperature of said sample steam in said sample conduit, measuring the total mass flow rate of the combined liquid and vapor components of said sample steam in said sample conduit, deriving the quality of said sample steam from an equation relating said measured sample steam pressure, pressure difference, temperature, and total mass flow rate to said sample steam quality, the desired quality of said line steam being substantially the same as the derived quality of said sample steam, measuring the pressure of said line steam in said steam line, measuring the pressure difference across said orifice in said steam line, measuring the temperature of said line steam in said steam line, and deriving the desired total mass flow rate of said line steam from an equation relating said measured line steam pressure, pressure differences, temperature, and the herein derived line steam quality to said total mass flow rate of said line steam.

7. Apparatus for determining the quality of steam containing both liquid and vapor components and flowing in an orifice-containing steam line comprising:

steam sampling means for drawing off through an orifice-containing sample conduit from said steam line a sample of said steam having substantially the same quality as said line steam, means for measuring the temperature in said sample conduit, means for measuring the static pressure in said sample conduit, means for measuring the differential pressure across said sample conduit orifice, and means connected to said sample conduit for measuring the two-phase mass flow rate of said drawn off sample of steam, such that said sample steam quality may be determined by means of an equation relating said measured sample conduit temperature, static pressure, differential pressure, and two-phase mass flow rate, said determined sample steam quality being substantially the same as said desired line steam quality.

8. Apparatus for determining the quality and the two-phase mass flow rate of steam containing both liquid and vapor components and flowing in an orifice-containing steam line comprising:

steam sampling means for drawing off through an orifice-containing sample conduit from said steam line a sample of said steam having substantially the same quality as said line steam, means for measuring the temperature in said sample conduit, means for measuring the static pressure in said sample conduit, means for measuring the differential pressure across said sample conduit orifice, means connected to said sample conduit for measuring the two-phase mass flow rate of said drawn off sample of steam, such that said sample steam quality may be determined by means of an equation relating said measured sample conduit temperature, static pressure, differential pressure, and two-phase mass flow rate, said determined sample steam quality being substantially the same as said desired line steam quality, means for measuring the temperature in said steam line, means for measuring the static pressure in said steam line, and means for measuring the differential pressure across said steam line orifice, such that said line steam two-phase mass flow rate may be determined by means of an equation relating said measured steam line temperature, static pressure, and differential pressure, and said line steam quality which is substantially the same as said determined sample steam quality.

9. Apparatus as in claim 8 wherein said steam sampling means comprises a sampling probe which takes a steam sample having substantially the same quality as said line steam, a sample conduit containing an orifice in a vertical portion through which the steam sample flows upwardly, and thermal insulation around said sampling means to maintain the sample steam quality substantially the same as said line steam quality, and said means for measuring the two-phase mass flow rate of said drawn off sample of saturated steam comprises a condenser connected to take the effluent from said steam sampling means and convert it all to the liquid phase and means to collect the condensed sample, means to determine the mass of the collected sample, and means to measure the time of collecting.

* * * * *